United States Patent [19]

Iglesias et al.

[11] Patent Number: 6,024,712

[45] Date of Patent: Feb. 15, 2000

[54] ORTHOPAEDIC DEVICES WITH PLASTIC INJECTION MOLDED ONTO FABRIC

[75] Inventors: Joseph M. Iglesias, Thousand Oaks; Tracy E. Grim, Camarillo; Stacy L. Wyatt, Ventura; John Bourne, Camarillo; Randa T. Milliken, Oxnard; Alec Bobroff, Santa Monica, all of Calif.

[73] Assignee: Royce Medical Company, Camarillo, Calif.

[21] Appl. No.: 09/018,318

[22] Filed: Feb. 3, 1998

Related U.S. Application Data

[63] Continuation-in-part of application No. 08/580,129, Dec. 28, 1995, Pat. No. 5,713,837.

[51] Int. Cl.⁷ .............................. A61F 5/00; A61F 13/00
[52] U.S. Cl. .................................................. 602/6; 602/27
[58] Field of Search ................... 602/6–8, 27–29, 602/65; 24/712.9, 712.7

[56] References Cited

U.S. PATENT DOCUMENTS

| | | |
|---|---|---|
| 667,768 | 2/1901 | De Puy . |
| 972,620 | 10/1910 | Hennessey ............................. 24/712.9 |
| 1,419,410 | 6/1922 | Robidoux ............................... 24/712.9 |
| 1,466,673 | 9/1923 | Solomon et al. ....................... 24/713.9 |
| 1,608,214 | 11/1926 | Janke ...................................... 24/712.9 |
| 3,298,365 | 1/1967 | Lewis ...................................... 602/27 X |
| 4,520,806 | 6/1985 | Miller . |
| 4,724,847 | 2/1988 | Nelson . |
| 4,768,502 | 9/1988 | Lee . |
| 4,825,856 | 5/1989 | Nelson . |
| 4,878,505 | 11/1989 | Thanner ................................. 128/882 |
| 5,093,067 | 3/1992 | Gibson . |
| 5,152,082 | 10/1992 | Culpepper ............................. 602/27 X |
| 5,154,690 | 10/1992 | Shiono .................................. 602/27 X |
| 5,307,521 | 5/1994 | Davis . |
| 5,370,133 | 12/1994 | Darby et al. ........................... 128/882 |
| 5,456,976 | 10/1995 | LaMarca, II et al. . |
| 5,647,150 | 7/1997 | Romanato et al. . |

FOREIGN PATENT DOCUMENTS

| | | |
|---|---|---|
| 0 234 341 | 9/1987 | European Pat. Off. . |
| 0 332 899 | 9/1989 | European Pat. Off. . |

*Primary Examiner*—Richard J. Apley
*Assistant Examiner*—Denise Pothier
*Attorney, Agent, or Firm*—Oppenheimer Wolff & Donnelly LLP

[57] ABSTRACT

The present invention pertains to an orthopedic support having a flexible inner member and an exo-skeleton that is molded directly onto the flexible inner member. In one particular embodiment, a versatile, multi-medium orthopedic ankle support assembly has an inner fabric support for extending at least partially around an injured part of the anatomy and for providing basic support for the injury. A plastic exo-support is injection molded into said fabric support and supplies supplemental support for resisting motion of the injured part in undesired directions. The fabric support has a main body portion for extending at least part way around the injured part of the anatomy and has edges to be secured together after the fabric support is fitted to the injured part. The invention is not limited to ankle braces, of course, as the general principle of molding an exo-skeleton onto a flexible inner member may be used in conjunction with numerous different supports. An efficient method for constructing an orthopedic support includes the steps of first placing a sheet of flexible material across a mold, cutting the sheet, injection molding the exo-structure onto the sheet material in the mold, and securing the sheet into an orthopedic support.

27 Claims, 8 Drawing Sheets

ORTHOPAEDIC DEVICES WITH PLASTIC INJECTION MOLDED ONTO FABRIC

I. RELATED APPLICATIONS

This is a continuation-in-part of U.S. patent application Ser. No. 08/580,129, which was filed Dec. 28, 1995, U.S. Pat. No. 5,713,837 and which is incorporated by reference herein.

II. BACKGROUND OF THE INVENTION

A. Field of the Invention

The present invention relates to orthopedic supports and, more particularly, to an orthopedic support that has a molded exo-structure.

B. Prior Art

There are a number of known ways to stiffen fabric orthopedic supports for injured parts of the anatomy. U.S. Pat. No. 4,724,847, for example, discloses an ankle brace that has a plurality of pockets. Rigid stay members are inserted into the pockets to form a rigid structure that surrounds and immobilizes the ankle. U.S. Pat. Nos. 3,298,365, 4,280,488, 4,825,856, and 4,440,158, among others, disclose similar arrangements.

A drawback of these designs is that they require a great deal of labor to construct. Workers must be hired to cut many separate pieces of fabric, sew the supports together, insert the rigid stays and so on. A further drawback is that the stays are typically die-cut from plastic of constant thickness. The shape of the stays is therefore quite limited, and the final support often does not fit the anatomy perfectly. While stays can be manufactured to have a particular contour, the manufacturing process is not simple and is often fairly expensive.

Efforts have been made outside of the orthopedic support art to create stiffened, custom-shaped objects by injecting hardenable material into a mold in which fabric has been placed. For example, European Patent Application No. 89103277.3, which the EPO published on Feb. 24, 1989 as publication number 0 332 899, discloses a diaphragm formed by injection molding plastic onto a piece of fabric. The diaphragm acts as a pressure barrier in an automobile engine. European Patent Application No. 87101406.4, published on Feb. 3, 1987 as publication no. 0 234 341, discloses creating fiber reinforced structures for automobiles. Fibrous material is placed into a mold, and then resin is injected into the mold. The resin saturates the fabric and eventually sets, thereby forming a reinforced automobile part. Other examples include U.S. Pat. Nos. 5,093,067 and 5,456,976.

U.S. Pat. No. 5,647,150, which issued Jul. 15, 1997, discloses forming a shoe by stretching a sock about a mold. A thermoplastic film layer is positioned between the mold and the fabric layer. Thermoplastic material is then allowed to flow through the fabric and bond with the thermoplastic film layer, thereby securing the thermoplastic material to the fabric. However, the method requires that the thermoplastic material flow entirely through the fabric in order to bond with the thermoplastic film layer on the opposite side of the fabric. The end result is a shoe with plastic on both the outside and the inside, and the shoe provides no cushioning between the molded plastic and the foot.

While the concept of injection molding plastic onto fabric substrates has been attempted in the automobile and shoe industries, the concept has not been developed to address the special problems associated with devices for treating injured portions of the body.

III. SUMMARY OF THE INVENTION

The object of the present invention is to advance the art with respect to orthopedic supports and to provide an improved method for manufacturing orthopedic supports.

Generally speaking, the present invention is an orthopedic support having a flexible inner member and an exo-skeleton that is molded directly onto the flexible inner member.

Considering one particular embodiment, a versatile, multi-medium orthopedic ankle support assembly has an inner fabric support for extending at least partially around an injured part of the anatomy and for providing basic support for the injury. A plastic exo-support is injection molded into said fabric support and supplies supplemental support for resisting motion of the injured part in undesired directions. The fabric support has a main body portion for extending at least part way around the injured part of the anatomy and has edges to be secured together after the fabric support is fitted to the injured part. The invention is not limited to ankle braces, of course, as the general principle of molding an exo-skeleton onto a flexible inner member may be used in conjunction with numerous different supports.

Considering additional features that may be present in particular embodiments, the plastic exo-support may have as a part thereof combined hooks and eyelets located along the edges for receiving laces for holding said support assembly in its desired firm supporting relationship with the injured part. With this arrangement, the user may lace up the support assembly using the eyelets or, alternatively, using the hooks for reliable rapid lacing of said support assembly into place.

Considering further additional features that may be incorporated into particular embodiments, the ankle brace embodiment may have an open heel portion. The exo-structure can also sewn onto the flexible material. The exo-support may have finger-like members for adapting to the anatomy of a particular ankle while providing adequate support. The finger-like members may extend from a common base, with a space between each of the finger members. Alternatively, the exo-support may be continuous, without fingers but with a contour that conforms to the portion of the anatomy to be supported.

The thickness of the exo-support may be increased or decreased in certain areas, to provide different levels of support and flexibility at different points on the support. The support may include speed laces, and the speed laces may either be an integral part of the exo-structure, or may be provided separately to be molded into the exo-structure or attached separately after the exo-structure is molded. The exo-structure may be adapted to receive a separate support member after molding. Also, the exo-structure may be molded over a stay or other member that is attached to the flexible material or otherwise introduced into the mold prior to injection molding.

The support may further comprise straps about which the exo-structure is injection molded, thereby attaching the straps to the support. The support may include one or more bladders, and may also include a pump for inflating the bladders. Alternatively, the support may include gel or foam pads.

The exo-structure may be molded from more than one type of material. For example, the exo-structure may be a more flexible material in one region where flexibility is desired, and a stiffer material in another region where greater stiffness is desired.

An efficient method for constructing an orthopedic support includes the steps of first placing a sheet of flexible material across a mold, cutting the sheet, injection molding the exo-structure onto the sheet material in the mold, and securing the sheet into an orthopedic support. The exo-structure may be molded from molten plastic, which may bond to the flexible material by melting the flexible material and/or by flowing through pores in the flexible material and then setting as the plastic cools. The method can be adapted to permit the plastic to extend only partially through the flexible material, to provide cushioning between the exo-structure and the injured portion of the body on which the support is to be placed.

Other objects and features of the invention will become apparent from a review of the Detailed Description below, from the drawings, and from the claims.

IV. BRIEF DESCRIPTION OF THE DRAWINGS

V. DETAILED DESCRIPTION OF THE PREFERRED EMBODIMENT

Figure 1:
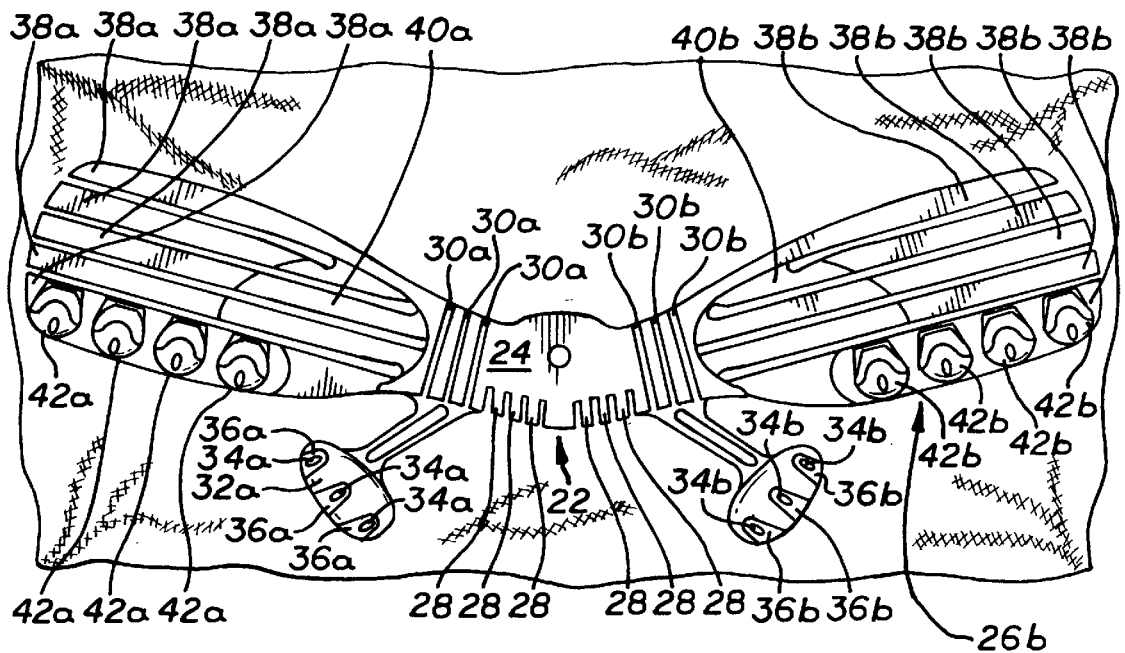
FIG. 1 is a perspective view of one embodiment of an ankle brace as it appears part way through the manufacturing process, according to the present invention.

FIG. 1 illustrates a sheet of flexible porous sheet material 20 onto which a semi-rigid plastic exo-structure 22 has been injection molded. To form the exo-structure 22, the sheet material 20 is stretched across an injection mold, which is then closed under normal hydraulic pressure. The edges of the sheet material 20 normally extend beyond the cavity of the mold (not-shown). Once the mold is hydraulically closed, the injection molding mechanism injects melted plastic into the mold to form the exo-structure 22. The melted plastic permeates the porous sheet material 20 and bonds to the sheet material 20 when it cools. Consequently, no additional securing means is necessary to attach the exo-structure 22 to the sheet material 20.

A variety of different materials may be used for both the sheet material 20 and the injection-molded exo-structure 22. For purposes of illustration but not limitation, the sheet material should be a material that is both suitable for use in an orthopedic support and which will allow the melted resin to permeate into it or through it. For example, the sheet material 20 may be a polypropylene knit material, a polyester knit or a nylon. Certain foam laminates and neoprene may be used in some applications. One material that has been used successfully is a polyester spacer fabric available from Gehring Textiles of New York.

The exo-structure may also be made from a variety of different thermoset and thermoplastic materials. Examples include polyethylenes, polypropylenes, thermoplastic eurethanes, TPE's and vinyls. Nylon or glass-filled nylon may be used in applications where the exo-structure must be stiff.

Further considering FIG. 1, the exo-structure 22 includes a heel portion 24 and two side supports 26a and 26b. The heel portion includes a plurality of cut-outs 28 that allow for conformability and fit. Channels 30a and 30b extend along either side of the heel portion 24. When the manufacturer folds the assembly into a finished ankle brace, such as that which FIG. 2 illustrates, the manufacturer may fold the brace along any of the channels 30a and 30b in order to size the heel.

The exo-structure of FIG. 1 includes two lacing extensions 32a and 32b. The extensions 32a and 32b include a thin portions through which extend a plurality of dorsal lace holes 34a and 34b, respectively. The thin portions extend to the edge of the extensions to provide wells 36a and 36b for a shoe lace.

The side supports 26a and 26b include a plurality of fingers 38a and 38b, respectively. The fingers stiffen the support, yet permit the support to adjust to the shape of the ankle and permit the support to flex somewhat during use. The thickness of the fingers may be varied to alter the performance of the support. In the particular embodiment that FIG. 1 illustrates, the exo-structure has a thin region 40 that makes the support more flexible in an area corresponding to the ankle. The support is then more comfortable, allowing for the brace to conform to the contours of the ankle bones in that area. The fingers 38a and 38b are thicker at the ends, away from the ankle, in order to stiffen the support where less flexibility and more support is desired.

Figure 4:
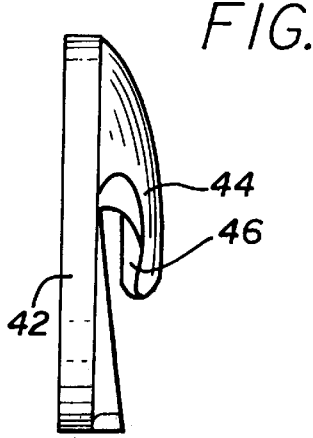
FIG. 4 is a side view of a speed lace of the embodiment of FIG. 1.
Figure 5:
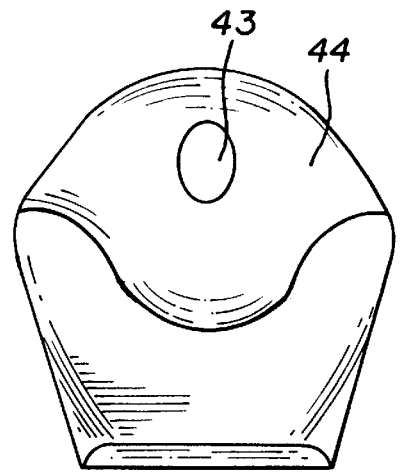
FIG. 5 is a is a top view of the speed lace of FIG. 4.
Figure 2:
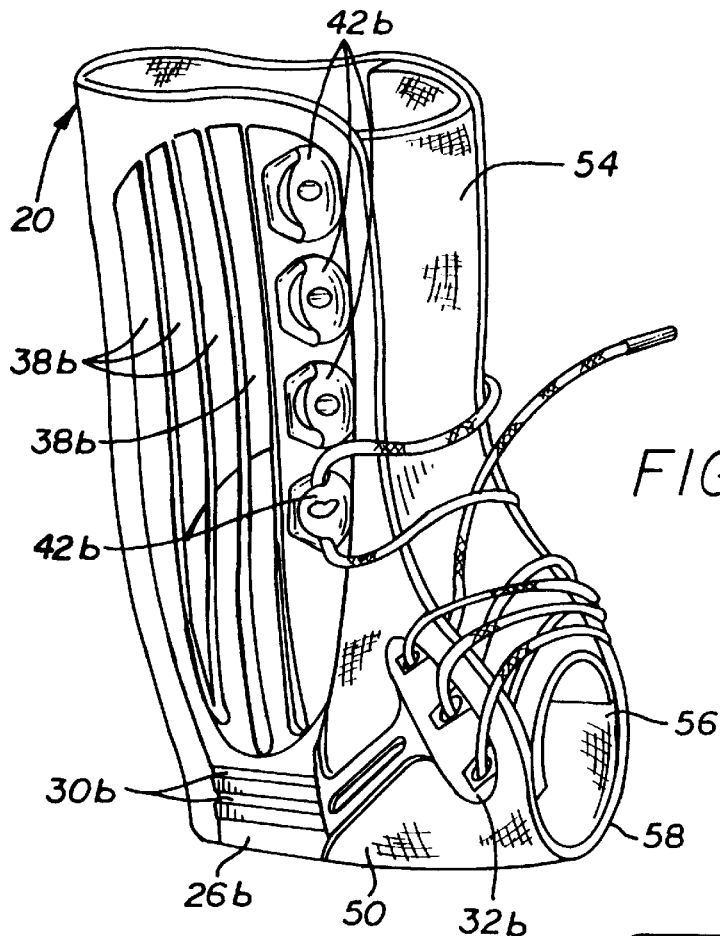
FIG. 2 is a side view of the ankle brace of FIG. 1.

The exo-structure of FIG. 1 also includes two sets of speed laces 42a and 42b, about which a lace can wrap, as FIG. 2 illustrates. The speed laces 42a and 42b also include lace apertures 43 (FIG. 5), which provide the end-user with the option of either wrapping the shoe lace about the speed laces to lace the support quickly, or running the lace through the lace apertures for very secure lacing. As FIGS. 4 and 5 illustrate, each speed lace has a portion 44 that extends up and over the plane of the rest of the exo-structure 22, providing a portion about which the lace may be wrapped. It should be known to those in the injection molding art that a special mechanism may be employed to form the speed laces. In particular, a spring-loaded lifter may be employed in the mold to automatically push a portion of the mold away from the protruding portion of the speed lace when the injection molding machine is opened.

Figure 6:
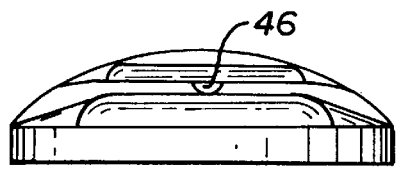
FIG. 6 is another side view of the speed lace of FIG. 6.

As FIGS. 4 and 6 illustrate, each of the speed laces may include a small rib 46 that provides tension to the lace during lace-up. The tension from the small rib prevents the lace from loosening. The rib acts to pinch the shoe lace when pulled into place, securing the lace by compression and friction. The width of the opening at the rib is less than the thickness of the lace, such that the lace is secured when pulled underneath the rib.

After the exo-structure 22 has been injection molded onto the sheet 20, the manufacturer can then form the exo-structure 22 and the sheet 20 into a support 48 (FIG. 2). The sheet 20 must first be cut, such as by die cutting, to form the outer body 50 of the support. The sheet 20 can be cut in a variety of different ways. The sheet 20 can be die-cut after the injection molding step. Alternatively, the mold can be designed to cut the sheet during the molding process. The sheet material can be stored on a roll, then fed from the roll to the mold for injection molding. As a further alternative, the sheet 20 can be cut in advance and held in place within the mold by means of hanging and locating pins.

Figure 3:
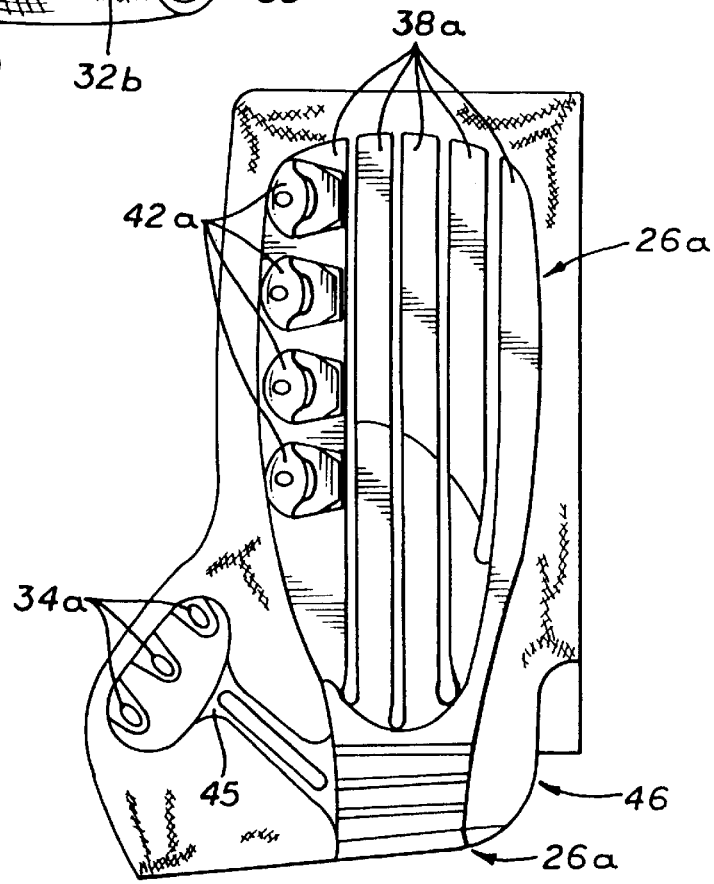
FIG. 3 illustrates a sheet of fabric onto which a plastic exo-structure has been injection molded, from which the embodiment of FIG. 1 is constructed.

Referring to FIG. 3, a heel opening 46 may be cut into the sheet material 20. The heel opening 46 allows the heel of the user to extend outside of the support, for added comfort and ventilation. A strip of binding material (not shown) may be sewn about the edges of the ankle hole to cover the cut edges and to prevent the edges from tearing. A small semi-circular piece of cushioning material (FIG. 3) may be attached to the inside rim of the heel opening 46. The small piece of cushioning material functions to cushion the top portion of the calcaneus.

Referring again to FIG. 2, a tongue 54 is secured to the support. The tongue 54 is typically made of a comfortable material such as neoprene or another foam, so that the tongue cushions the pressure from the laces. The tongue is typically sewn onto the support, but may be attached in other ways conventional in the art.

The support may include an inner liner 56 made from a flexible, porous material that provides breathability and compression. The inner liner 56 may be a thin sheet of polyester spacer fabric. The inner liner 56 may be sewn onto the support, either directly or in conjunction with a thin strip of binding material 58 at the edge of the support.

Figure 7:
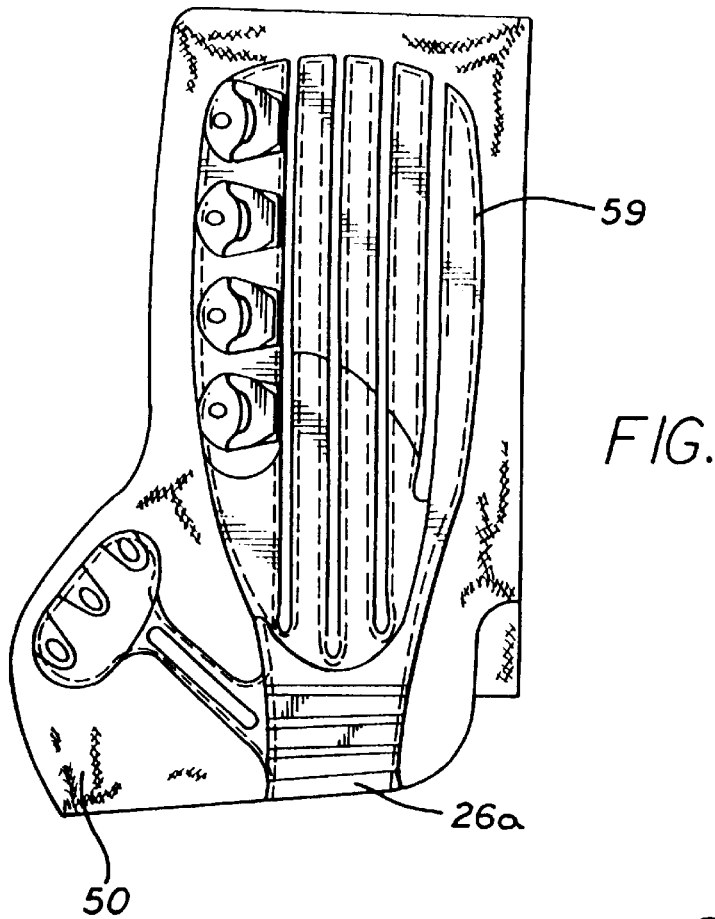
FIG. 7 is a side view of an additional embodiment of an ankle brace in which the exo-structure is both injection molded and sewn onto the fabric for added reinforcement.

FIG. 7 illustrates an alternative embodiment in which the exo-structure 22 is sewn onto the sheet material 20. The exo-structure may be formed separately and then sewn onto the sheet material. Alternatively, the exo-structure 22 may first be injection molded onto the sheet material 20, as described above, then sewn as with sew lines 59 for reinforcement. If the exo-structure is first injection-molded onto the sheet material 20, the sewing serves to reinforce the bond between the exo-structure and the sheet that already exists. As an alternative or a supplement to sewing, various solvent based adhesives can be introduced onto the material prior to injection molding. The adhesive then acts to further bind the exo-structure to the sheet. However, it should be noted that in the presently preferred embodiment, the injection molding process itself binds the exo-structure to the sheet, so that no additional adhesive or sewing is needed to secure the exo-structure to the sheet.

The sets of fingers 38a and 38b of the embodiment of FIG. 2 help conform the support to the shape of the ankle. The fingers allow the support to adapt to a swollen ankle, for example, and to adjust the shape as the swelling goes down. The fingers provide longitudinal support while allowing for compression. The fingers in the embodiment of FIG. 2 get thinner in the region 40 close to the ankle, which is typically tender when the ankle is injured, in order to minimize pressure points. The fingers are thicker away from the ankle in order to provide additional support.

Figure 8:
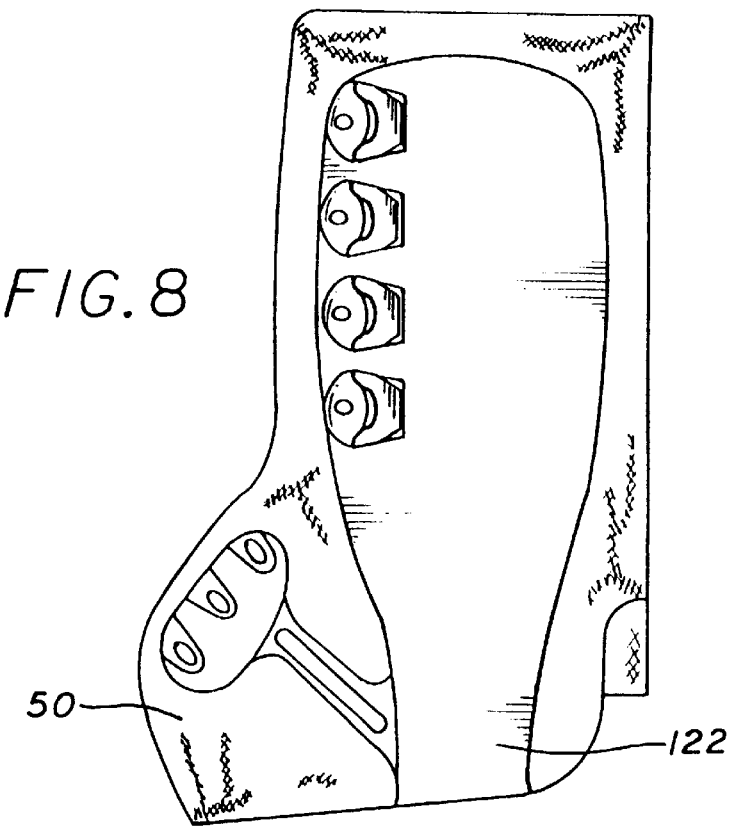
FIG. 8 is a side view of an additional embodiment in which the exo-skeleton does not have the fingers of the embodiment of FIG. 1.

The embodiment of FIG. 8 provides an alternative to the fingers of FIG. 2. The exo-structure 122 is continuous. Rather than having fingers that adapt to the shape of the ankle, the exo-structure 122 is contoured to fit the ankle. As with the embodiment of FIG. 2, the exo-structure 122 of FIG. 8 is formed in standard injection-molding equipment and is injection molded directly onto the underlying flexible sheet material.

Figure 9:
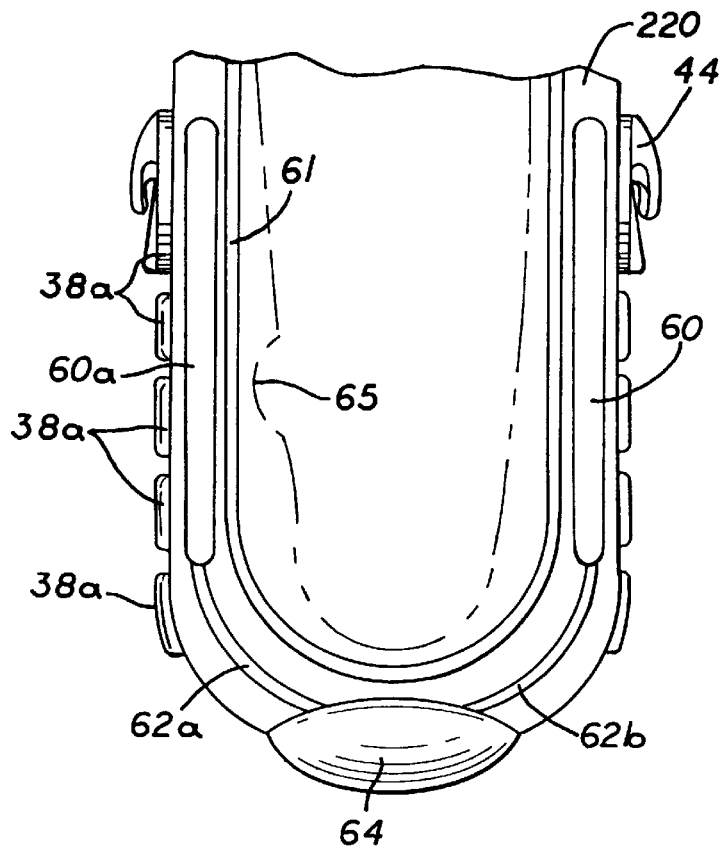
FIG. 9 is a cross-sectional view of an embodiment having a pump and bladders.
Figure 10:
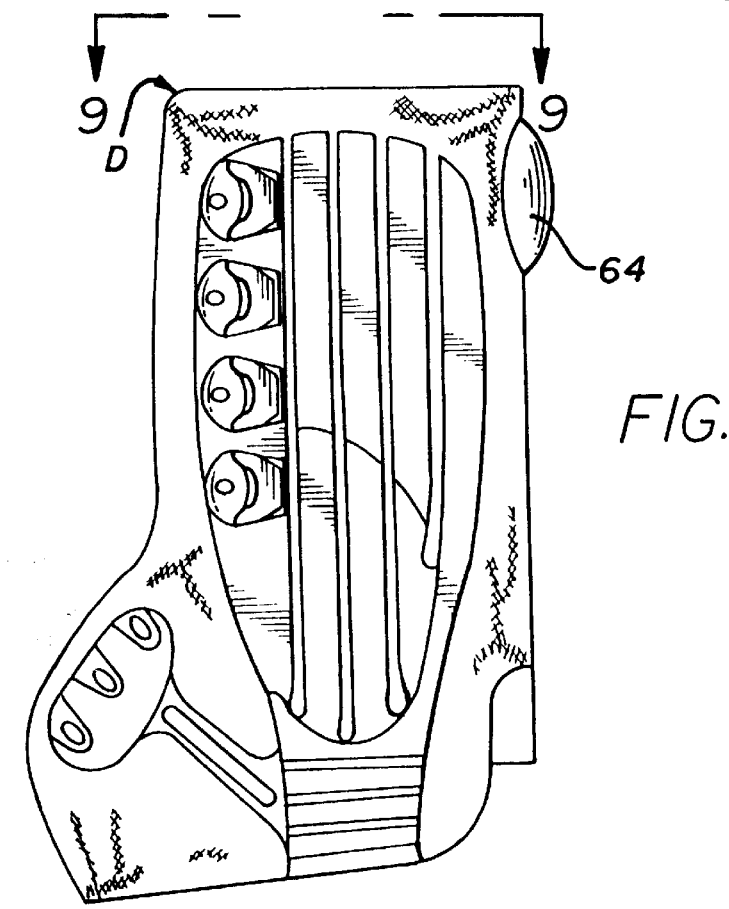
FIG. 10 is a side view of the embodiment of FIG. 9.

Embodiments of the present invention may include one or more bladders. FIGS. 9 and 10 illustrate an embodiment having bladders 60a and 60b embedded in the walls of the support. Bladders embedded in the wall of a support are conventional in the art. However, the embodiment of FIG. 9 also has an injection-molded exo-structure 22 on the outside of the support, which is a feature of the present invention.

The embodiment of FIG. 9 includes the two bladders 60a and 60b, an inner liner 61, and tubes 62a and 62b extending from a respective bladder to a pneumatic bulb pump 64. To inflate the bladders, the user repeatedly presses the bulb pump 64. Each bladder will normally be provided with a valve that prevents air from escaping from the inflated bladder through the tubes 62a and 62b, in order to maintain the inflation of the bladders. The bladders serve to provide additional support to the ankle 65. A conventional release valve is provided in conjunction with each of the bladders to selectively let pressure out of the bladders when they are inflated.

The bladders are normally formed within the sheet material 220 prior to injection-molding the exo-structure onto the sheet material. However, alternative arrangements are possible in which, for example, the bladder and tubing is inserted into the sheet material 220 after the exo-structure has been formed. In many embodiments, the bladders will go in between the sheet material 220 and the inner liner. While the bladders are generally air-filled, they may be filled with foam instead of, or in addition to, air under pressure.

As an alternative to the air bladders of FIG. 9, the support may be provided with gel pads. The walls of the support may be provided with pouches into which the gel pads are inserted after the injection molding has already been completed. The gel pads either would be placed next to the skin, between the ankle and the inner liner, or would be sandwiched between the outer layer 220 and the inner liner. With this arrangement, the support may be used for hot/cold therapy, in which hot and/or cold gel packs are inserted into the support.

Figure 11:
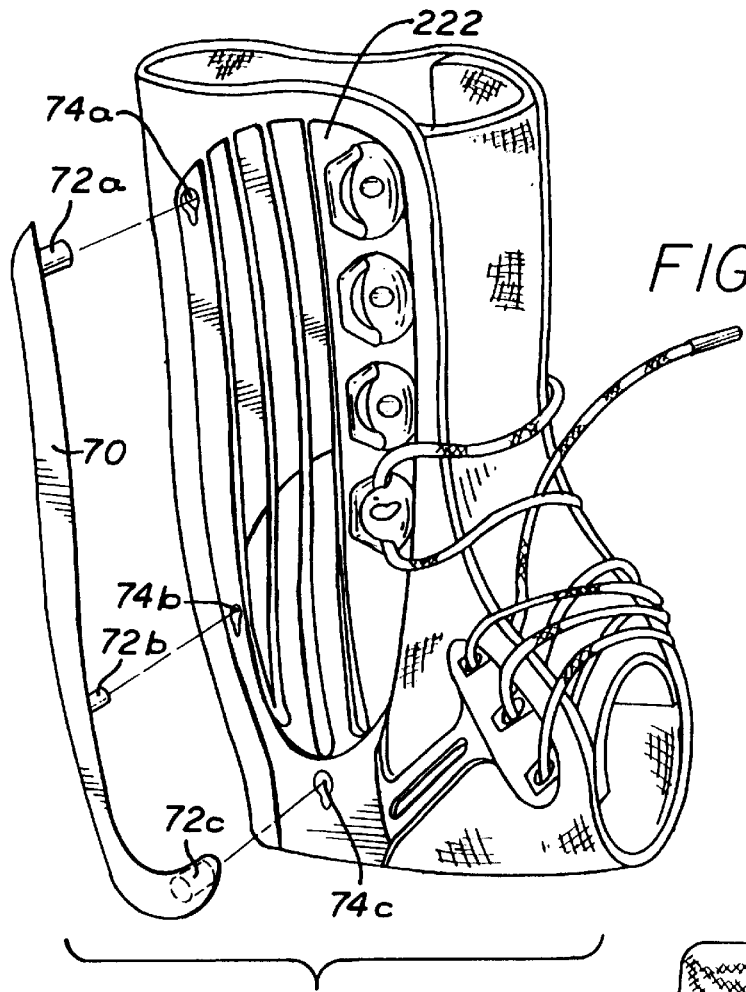
FIG. 11 is a perspective view of an ankle brace having a removable stay so that the user can vary the stiffness of the brace.

In some applications it may be desired to further stiffen the exo-structure. Consequently, the embodiment of FIG. 11 is designed to permit the user to selectively add and remove an additional frame member 70. The frame member 70 has posts 72a, b and c which may be inserted into compatible apertures 74a, b, c to removably secure the frame member 70 to the exo-structure. The presently preferred frame member 70 is injection-molded plastic, although the frame member could be made from a wide variety of materials, including metals for extra stiffness.

The concept of adding structural members that FIG. 11 illustrates can be extended beyond merely adding an additional frame member 70. Other structural components, such as pads, stays, electronic devices and any other attachment suitable for attachment to an orthopedic support may be attached to the exo-structure and/or the flexible sheet material.

Figure 12A:
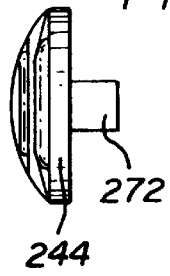
FIGS. 12A and 12B are embodiments of speed laces that may be used in conjunction with the embodiment of FIG. 12.
Figure 12B:
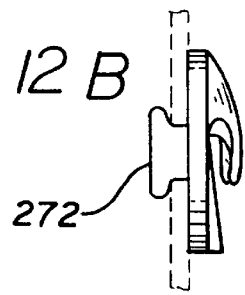
Figure 12:
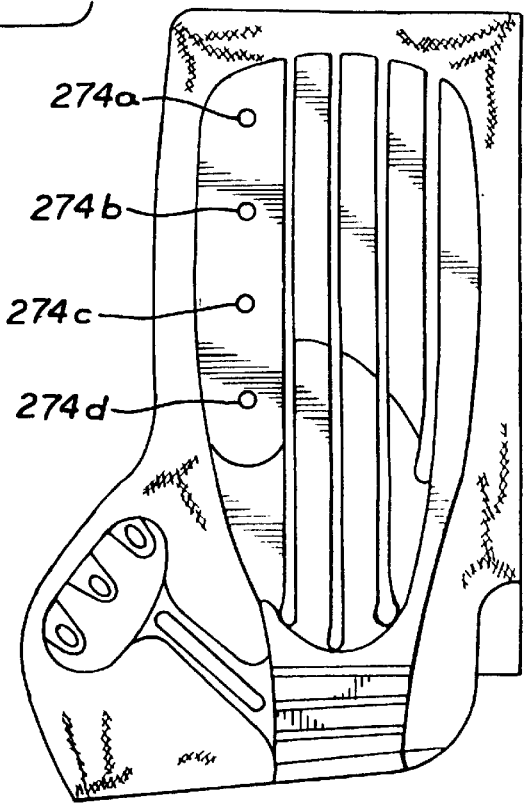
FIG. 12 is a side view of a further embodiment in which the speed laces are attached after the exo-structure has been injection molded onto the fabric.

For example, the speed laces may be formed separately and attached after the exo-structure has been injection molded. FIG. 12 illustrates such an arrangement, with attachable speed laces 244 (FIG. 12A) each having a post 272 to insert into a mating aperture, such as apertures 274a–d. An alternative post 272' may be employed, in which the post includes a knob 276 that allows the speed lace 244' to snap into the exo-structure. By attaching them to the exo-structure separately, the speed laces may be made from a different material than the exo-structure. For example, the speed laces may be formed of a harder, more durable material than the exo-structure, which might be made of a more flexible material. In addition to snapping into place as FIG. 12B illustrates, the speed laces may be attached by other known means, such as sonic welding or riveting.

Another embodiment of the present invention involves over-molding an exo-skeletal semi-rigid plastic framework over a more rigid plastic material. The more rigid plastic piece is either pre-injection molded or die-cut and then placed into the mold along with the fabric material. The more rigid plastic piece may also be pre-injection molded onto the fabric material. The exo-skeletal material may then be formed of a softer material for better comfort, with the more rigid plastic material providing the rigidity. The exo-skeletal material is injection molded over the more rigid plastic material and onto the fabric.

Figure 13:
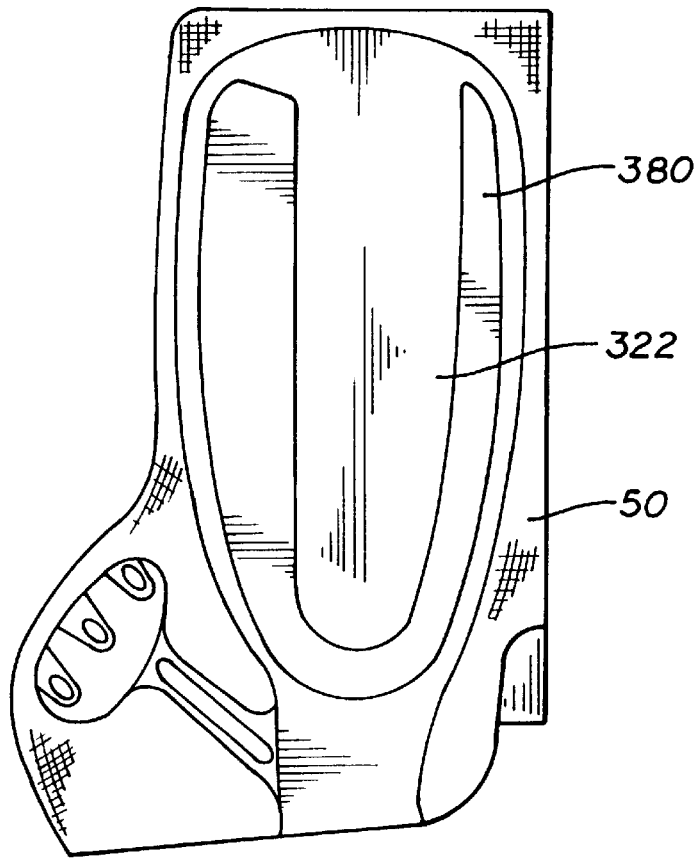
FIG. 13 is a side view of a further embodiment in which the exo-structure is molded over a stay member.

Referring to the embodiment of FIG. 13, the exo-skeletal semi-rigid plastic framework 322 is molded over a plastic stay member 380 that is made of a more rigid plastic or metal material. The stay member 380 can be pre-injection molded by itself or onto the flexible sheet material 20. In either case, both the stay member 380 and the fabric sheet are placed (separately or pre-attached) together in the injection mold. The exo-structure 322 is then injection molded onto the sheet and over the stay member 380.

Figure 14:
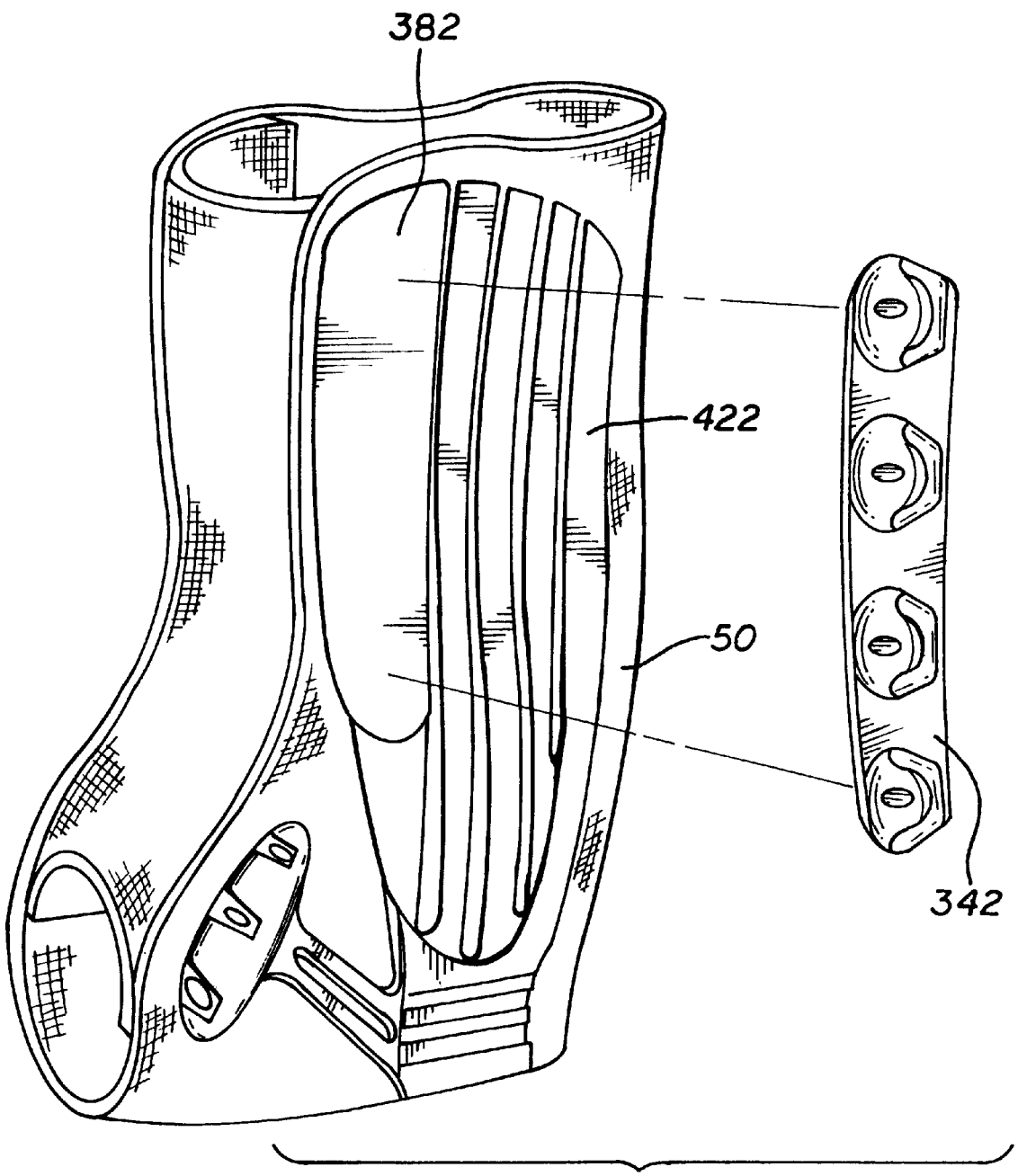
FIG. 14 is a further embodiment in which the speed laces are provided in a separate assembly.
Figure 15:
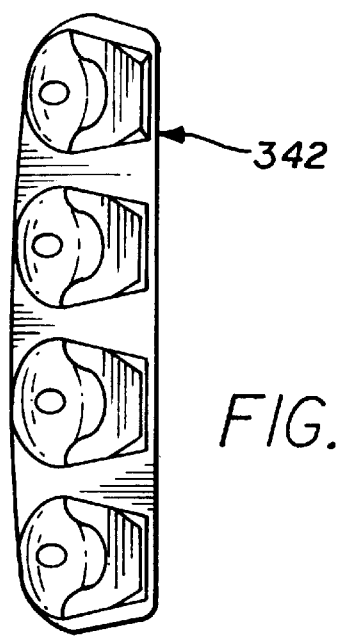
FIGS. 15 and 16 are top and side views, respectively, of a speed lace assembly that may be used in conjunction with FIG. 14.
Figure 16:
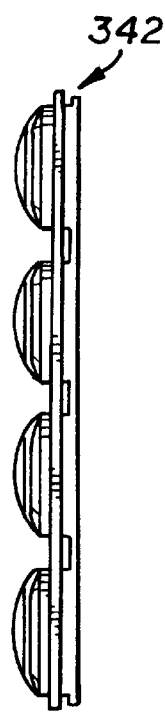

This concept can be extended to molding an exo-structure about a pre-fabricated speed lace assembly. The speed laces may be molded with a thin base of plastic (FIGS. 14, 15 and 16). The speed lace assembly 342 is then placed in the injection mold along with the flexible sheet material The exo-structure plastic is then injection molded on to the fabric and over the speed lace assembly, thereby bonding the speed lace assembly in place. Alternatively, the speed lace assembly may be attached at a predetermined area 382 after the exo-structure 422 is formed, by means of welding, an adhesive, and/or other attachment means known in the art. (FIG. 14).

Figure 17:
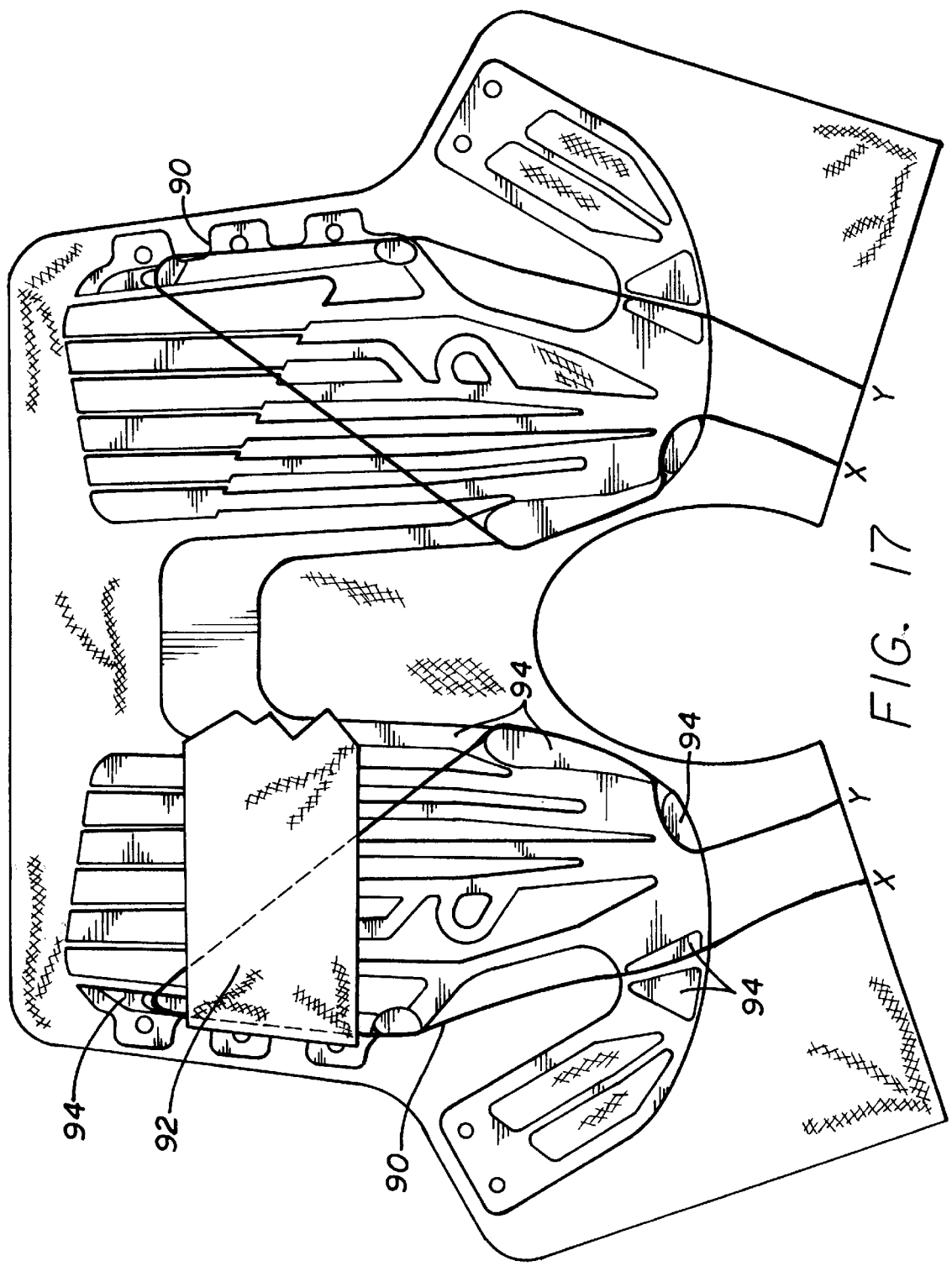
FIG. 17 is an embodiment having a cable support system.

The foregoing has described a presently preferred embodiment of the invention, as well as alternative embodiments. However, it should be understood that the scope of the invention is not limited to what is described in the Detailed Description. Numerous variations may be employed within the scope of the invention. For example, as illustrated in FIG. 17, an orthopedic support according to the present invention may include a cable reinforcement system over the exo-skeletal framework to provide additional medial/lateral support and compression. The cable 90 may be a single filament line, for example, that interacts with the lacing and/or strapping system. When the laces or straps are tightened they pull the single filament wire 90 taut. For example, in FIG. 17, a strap 92 pulls the wire 90 taut when tightened. A system of guides 94 may be molded as part of the exo-structure, and the cable 90 may pass through the guides.

The support may be fitted with various attachments and hardware. For example, the exo-structure may be molded to include pins, channels, grooves, pockets and the like in which attachments such as stays, stiffeners, pipes, electronic and/or magnetic devices, gel pads, heaters, coolers, medicine delivery mechanisms, and a variety of other devices may be mounted. In certain applications, electric wiring and/or electronic devices may be added into the mold prior to molding, with the exo-structure being injection molded over or around the electric and/or electronic devices.

Similarly, the orthopedic support may be modified for use in particular climates, such as by adding insulating pads and/or layers to the support for use in cold weather. The heel portion may also be closed rather than open in particular applications. Apertures may be cut into the sheet material for added ventilation in hot weather.

Hook and loop material may be added to the support to replace or supplement the laces, and various other changes may be made, within the scope of the invention. In another embodiment, straps are permanently attached during the injection molding process. The straps are placed in the injection mold with the porous sheet material. When the exo-skeletal framework is injection molded onto the sheet material, the straps are permanently molded into place. In some embodiments, three-dimensional shapes may be introduced into the mold to form three-dimensional finished products, such as certain thumb braces, wrist, and other braces having complex shape. As yet another alternative, the exo-structure may be formed on the interior side of the support rather than on the exterior, then covered with a soft liner before applying the support to the injured portion of the anatomy. The present invention can also extend to applications beyond orthopedic supports, such as devices for horses and other animals and protective pads for athletes.

The preferred method of manufacturing most embodiments of the present invention is with injection molding, in which a thermoplastic or thermoset material is heated and then injected into a mold. However, other approaches may be used as well. For example, an exo-structure may be formed onto a flexible sheet by placing the sheet across or into a mold, then closing the mold, then pouring a liquid resin that is at room temperature (or slightly heated) into the mold and allowing the resin to dry onto and to bond to the flexible sheet material to form the exo-structure.

The exo-structure is normally injection molded onto the flexible sheet material. However, instead of injection molding the exo-structure onto the flexible material, the exo-structure may be removably attached to the underlying flexible material with Velcro, snaps, and/or other conventional attachment means. The flexible underlying material may also be provided with pockets, slits or the like into which the exo-structure may be inserted and which will removably hold the exo-structure in place on the support.

The drawings illustrate various means for holding the support member and cushioning material to the portion of the anatomy to be supported. Such means are not limited to what is illustrated in the drawings however, as the support member and cushioning material can be held to the portion of the anatomy with straps, laces, and any other means that is conventional in the ankle brace art.

Accordingly, the present invention is not limited precisely to the arrangements as shown in the drawings and as described in detail hereinabove.

What is claimed is:

1. A versatile orthopedic ankle support assembly comprising:
   an inner fabric support for extending at least partially around an injured part of the anatomy and for providing basic support for the injury;

a plastic exo-structure injection molded into said fabric support and supplying supplemental support for resisting motion of said injured part in undesired directions;

said fabric support having a main body portion for extending at least part way around the injured part of the anatomy and having edges to be secured together after the fabric support is fitted to the injured part; and said plastic exo-structure having as a part thereof combined hooks and eyelets located along said edges for receiving laces for holding said support assembly in its desired firm supporting relationship with said injured part;

whereby the user may lace up said support assembly using either eyelets or, alternatively, using said hooks for reliable rapid lacing of said support assembly into place.

2. An orthopedic support as defined in claim 1, wherein said support is an ankle support having an open heel portion.

3. An orthopedic support as defined in claim 1, wherein said exo-structure is also sewn onto said fabric support.

4. An orthopedic support as defined in claim 1, wherein said exo-structure comprises finger-like members.

5. An orthopedic support as defined in claim 4, wherein said the thickness of said exo-structure is non-uniform to provide different levels of support at different points on the support.

6. An orthopedic support as defined in claim 1, wherein said combined hooks and eyelets are attached to said exo-structure as at least one piece separate from said exo-structure.

7. An orthopedic support as defined in claim 1, wherein said exo-structure is substantially continuous.

8. An orthopedic support as defined in claim 1, wherein said support further comprises a separate support piece that is adapted to attach to the exo-structure after injection molding to further stiffen the exo-structure.

9. An orthopedic support as defined in claim 1, wherein said support further comprises a stay on said flexible material over which said exo-structure is molded.

10. An orthopedic support as defined in claim 1, wherein said support further comprises straps about which the exo-structure is injection molded, thereby securing the straps to the support.

11. An orthopedic support as defined in claim 1, wherein said support further comprises at least one bladder.

12. An orthopedic support as defined in claim 11, wherein said support further comprises a pump that is in communication with said bladder.

13. An orthopedic support as defined in claim 1, wherein said exo-structure comprises plastics of different densities.

14. An orthopedic support for supporting an injured portion of the anatomy comprising:

flexible cushioning sheet material that is adapted to extend at least partially about the injured portion of the anatomy that is to be supported;

a plastic exo-structure that is injection molded onto said flexible sheet material to stiffen said support, the plastic of the exo-structure extending only partially through said flexible cushioning sheet material to provide cushioning between said exo-structure and the injured portion of the anatomy;

said support assembly including arrangements to hold the support around the injured portion of the anatomy;

said sheet material being formed into an orthopedic support after the exo-structure has been injection molded onto the sheet material.

15. An orthopedic support as defined in claim 14, wherein said support is an ankle support having an open heel portion.

16. An orthopedic support as defined in claim 14, wherein said exo-structure comprises finger-like members.

17. An orthopedic support as defined in claim 14, wherein the thickness of said exo-structure is non-uniform to provide different levels of support at different points on the support.

18. An orthopedic support as defined in claim 14, wherein said exo-structure includes line guides and said support further comprises at least one line that extends about said line guides to further reinforce said support.

19. An orthopedic support as defined in claim 14, further comprising a plurality of speed laces each having a lace hole, thereby providing a user with the option between lacing laces around the speed laces or through the lace holes.

20. An orthopedic support as defined in claim 14, wherein said arrangements to hold said support comprise laces.

21. An orthopedic support as defined in claim 14, wherein said arrangements to hold said support comprise hook and loop material.

22. An orthopedic support as defined in claim 14, wherein said arrangements to hold said support comprise straps.

23. An orthopedic support for supporting a portion of the anatomy comprising:

a flexible, porous outer shell having inner and outer surfaces; and a semi-rigid plastic exo-skeletal framework injection molded onto the outer surface of said outer shell, said exo-skeletal framework being permanently bonded to the outer shell from the injection molding;

wherein said exo-skeletal framework comprises a plurality of finger-like members, at least some of which are substantially parallel to one another, to provide support while conforming to the shape of the portion of the anatomy.

24. An orthopedic support as defined in claim 23, wherein said support is an ankle support and further comprises a tongue.

25. An orthopedic support as defined in claim 23, further comprising a plurality of speed laces having a lace hole, thereby providing a user with the option between lacing laces around the speed laces or through the lace hole.

26. An orthopedic support as defined in claim 23, wherein the exo-structure comprises a plurality of different plastics of different densities.

27. An orthopedic support for supporting a portion of the anatomy comprising:

flexible porous sheet material that is adapted to extend at least partially about the portion of the anatomy that is to be supported;

a plastic exo-structure that is injection molded onto said flexible sheet material to stiffen said support, the plastic of the exo-structure extending at least partially through said flexible cushioning sheet material to provide a fabric surface between said exo-structure and the portion of the anatomy; and said support assembly including arrangements to hold the support around the portion of the anatomy.

* * * * *